United States Patent
Mallow et al.

(10) Patent No.: US 6,231,650 B1
(45) Date of Patent: May 15, 2001

(54) BIOCIDAL COATING COMPOSITION

(75) Inventors: William A. Mallow, San Antonio, TX (US); Bryan Glynson, New York, NY (US); Larry Rogers, Half Moon Bay, CA (US)

(73) Assignee: Alistagen Corporation, New York, NY (US)

( * ) Notice: Subject to any disclaimer, the term of this patent is extended or adjusted under 35 U.S.C. 154(b) by 0 days.

(21) Appl. No.: 09/398,632

(22) Filed: Sep. 17, 1999

(51) Int. Cl.[7] .................................................. C09D 5/14
(52) U.S. Cl. .................. 106/15.05; 106/16; 106/792; 106/795; 106/805
(58) Field of Search ................................. 106/15.05, 16, 106/792, 795, 805

(56) References Cited

U.S. PATENT DOCUMENTS

| | | |
|---|---|---|
| 1,607,472 | 11/1926 | Mathers et al. . |
| 3,090,603 | 6/1963 | Gilchrist . |
| 3,120,444 | 2/1964 | Dunton et al. . |
| 3,808,740 | 5/1974 | Porter et al. . |
| 3,936,311 | 2/1976 | Kirst et al. . |
| 3,963,507 | 6/1976 | Kuramoto et al. . |
| 4,367,609 | 1/1983 | Lloyd et al. . |
| 4,946,685 | 8/1990 | Edgren . |
| 5,236,496 | 8/1993 | Shibuya et al. . |
| 5,277,712 | 1/1994 | McInnis ................. 106/774 |
| 5,334,243 | 8/1994 | Hyman ................... 106/794 |
| 5,346,542 | 9/1994 | Yosuke et al. .......... 106/194 |
| 5,372,642 | 12/1994 | Bartz et al. ............. 106/730 |
| 5,411,746 | 5/1995 | Signorino et al. ...... 424/464 |
| 5,482,543 | 1/1996 | Bleve et al. ............ 106/14.05 |
| 5,538,553 | 7/1996 | Burgand ................. 106/795 |
| 6,042,638 * | 3/2000 | Mallow et al. ......... 106/15.05 |

FOREIGN PATENT DOCUMENTS

| | | |
|---|---|---|
| 9104124 | 4/1993 | (BR) . |
| 261655 | 5/1989 | (CS) . |
| 1222413 * | 4/1960 | (DE) . |
| 2046046 | 3/1972 | (DE) . |
| 2200163 | 7/1973 | (DE) . |
| 2407622 | 8/1974 | (DE) . |
| 3529823 | 8/1985 | (DE) . |
| 054175 | 6/1982 | (EP) . |
| 464545 | 1/1992 | (EP) . |
| 530768 | 3/1993 | (EP) . |
| 669378 | 8/1995 | (EP) . |
| 2207964 | 6/1974 | (FR) . |
| 519547 | 3/1940 | (GB) . |
| 1522480 | 8/1978 | (GB) . |
| 55-144061 | 11/1980 | (JP) . |
| 55-144061 | 11/1981 | (JP) . |
| 57-046390 | 10/1982 | (JP) . |
| 0115055 | 7/1983 | (JP) . |
| 55090451 | 7/1987 | (JP) . |
| 62-019241 | 11/1987 | (JP) . |
| 3162478 | 7/1991 | (JP) . |
| 3296555 | 12/1991 | (JP) . |
| 64000972 | 8/1964 | (NL) . |
| 372507 | 12/1974 | (SE) . |
| 602524 | 3/1978 | (SU) . |
| 715598 | 2/1980 | (SU) . |
| 1098915 * | 6/1984 | (SU) . |
| 1247364 * | 7/1986 | (SU) . |

OTHER PUBLICATIONS

"Impact of Physical Properties of Slaked Line for Plastics by blending with Non–Ionic High Polymers" Sakada et al. Siekko to Sekka (1970).

* cited by examiner

Primary Examiner—Paul Marcantoni
(74) Attorney, Agent, or Firm—John L. Sigalos

(57) ABSTRACT

The present invention prolongs the biocidal activity of hydrated lime in a paint or coating by using a sufficient amount of a binder in the paint or coating to block carbon dioxide from reacting with the hydrated lime while still producing a coating that is durable and adhesive upon drying and not unduly friable due to the amount of hydrated lime in said coating.

18 Claims, No Drawings

BIOCIDAL COATING COMPOSITION

FIELD OF THE INVENTION

The present invention relates to hydrated lime coatings. More particularly, the invention relates to the first safe, non-toxic hydrated lime coatings, or paints, that resist degradation by carbon dioxide for prolonged periods of time.

BACKGROUND OF THE INVENTION

Hydrated lime coatings or paints are well known as disinfectants, biocidal, and biostatic agents. In order to retain their biocidal activity after application to a desired surface, a hydrated lime coating must retain (1) the ability to pull in and substantially encapsulate a microorganism, and (2) the alkalinity necessary to kill microorganisms. In order to kill microorganisms, the lime must have a pH between about 11–13. In order to retain the alkalinity necessary to kill microorganisms, the coating, or paint, must be protected from attack by carbon dioxide.

Unfortunately, hydrated lime is highly susceptible to environmental attack, primarily by carbon dioxide. Carbon dioxide converts the hydrated lime to calcium carbonate, which does not have the alkalinity required to kill microorganisms. As a result, conventional coatings or paints containing hydrated lime are not effective as long term disinfectants, biocides, or biostatic agents.

A means is needed to prolong the biocidal activity of a hydrated lime coating.

SUMMARY OF THE INVENTION

The present invention provides a biocidal coating comprising a first amount of hydrated lime and a binder comprising a cellulose derivative selected from the group consisting of an alkyl derivative, a hydroxyl derivative, and a carboxyl derivative. The binder has film properties of a barrier for carbon dioxide but not film properties of a barrier for water vapor, said binder being present in a second amount effective to render the coating durable and adhesive upon drying and to prevent a substantial increase in friability of said coating due to the first amount of hydrated lime in the coating.

DETAILED DESCRIPTION OF THE INVENTION

There has been a long felt but unsolved need for a hydrated lime paint or coating which was safe for public use, and which would last for longer than traditional white washes—which maintain biocidal activity for only about 1–2 weeks. The present invention involves the discovery that-when certain binders are used in a coating containing hydrated lime at a sufficiently high concentration, the binders will block the passage of carbon dioxide into the coating, preventing carbon dioxide from reacting with lime either in the coating itself, or in an underlying substrate. The binders also surprisingly are compatible with hydrated lime, and render the coating durable and adhesive upon drying.

The biocidal coating of this invention is non-toxic and maintains an alkalinity effective to kill microorganisms after one month exposure to 100% carbon dioxide, which would completely carbonate hydrated lime in a conventional lime coating in 1–2 days. As used herein, the term "one month of exposure to carbon dioxide" is defined to refer to exposure to 100% carbon dioxide for two days, as described in Example 2. In fact, the biocidal coatings maintain their biocidal activity for an indefinite period of time, even when aged in 100% carbon dioxide, as demonstrated in Example 2. The coatings exhibit slight changes during the first month of exposure to air in the atmosphere, and then stabilize. A typical coating formulation has maintained approximately 70% of its biocidal activity for nearly four years after application and exposure to atmospheric conditions.

By preventing the carbonation of lime in a biocidal coating, the binder prolongs the biocidal lifetime of the coating. The coating also may be used to prevent the carbonation of lime in Portland cement and concrete. When used in this manner, the binder prolongs the structural life of the cement by preventing the corrosion of the reinforcing steel rebars. Where the coating will be used to prevent carbonation of lime in cement, the coating may or may not contain the hydrated lime. While it may be desirable for the coating to contain the hydrated lime in order to obtain the additional biostatic advantages, the lime in the cement would be protected as long as the coating contains a sufficient amount of the binder, typically 10–30 parts by weight, preferably about 20 parts by weight (which represents 10–20 parts by weight of the dried coating).

The most important ingredients in a biocidal coating are the binder and the lime. A biocidal coating preferably comprises the following materials in an appropriate solvent: hydrated lime; a binder; a humectant; and, a filler. Preferably, the coating further comprises pigment, a surfactant, and an antifoaming agent. In some embodiments, it may be desirable to add a plasticizer. The binders of the present invention exhibit unexpected carbon dioxide barrier properties, UV resistance, and extended biocidal activity. The coatings of the present invention are safe, easy to prepare, and contain low cost materials, making the coating easily affordable by medical, agricultural, industrial, and domestic users alike.

The solvent or vehicle for the coating materials and binder may be aqueous or organic. The choice of solvent will depend upon the conditions that the coated item will encounter. For example, if the coating will be exposed to outdoor conditions, or if the coating will be exposed to repeated washings, then an organic solvent based binder may be preferred. The amount of solvent or vehicle used to make the coating is dependent upon the method of application desired. Preferably, the solvent or vehicle should be used in an amount sufficient to make the coating a spreadable fluid.

The binder is essential to the operation of the present invention. The binder should have the film properties of a carbon dioxide barrier, but should not act as a water vapor barrier. Carbon dioxide essentially should be blocked from reacting with the hydrated lime to form calcium carbonate. Water vapor should be able to permeate into the film to maintain a moisture content sufficient to (1) pull in and substantially encapsulate microorganisms and other biological contaminants, and (2) maintain hydroxyl ions in the lime in an ionized, highly alkaline state so that the lime will kill or otherwise render biological contaminants innocuous.

Certain binders are chemically incompatible with hydrated lime, and should not be used in the present invention. These incompatible binders include most latex binders, especially pH sensitive latices, which result in coagulation and phase separation almost immediately upon blending with lime. Other incompatible binders are water soluble film forming binders such as certain polyalcohols, polyesters, proteins, and starch derived carbohydrates. Many of these binders are unstable in aqueous lime systems, and typically result in mixtures having viscosities that change steadily with time and that frequently even solidify. Suitable binders should offer chemical compatibility with hydrated lime, desired adhesive and coating properties, and the required barrier properties. Preferred binders are cellulose derivatives selected from the group consisting of an alkyl derivative, a hydroxyl derivative, and a carboxyl derivative. Most preferred binders are ethylcellulose and hydroxy propylmethyl cellulose.

The ratio of binder to lime in the coating is an important feature of the coating. If the lime ratio is increased, the coating will have higher biocidal activity, but will be more friable. If the binder ratio is increased, the coating will be less friable, but the biocidal activity of the coating will decrease. Preferred formulas are given below for both a water base and an organic base coating. Regardless of the type of solvent, the amount of binder used should be sufficient to prevent carbonation of the lime and to maintain the biocidal activity of the coating for at least about "one month of exposure to carbon dioxide," preferably enough binder to last for four years or more. Typically, the lime:binder ratio is in the range of from about 1:1 to about 3:1, preferably about 1.5:1.

The coatings should have a consistency which is flowable for application, but the formula should permit the coating to dry over a reasonable period of time, preferably no longer than overnight. Preferably, the coatings of the present invention are applied to a thickness of between about 2–5 mil; however, the coating may have substantially any desired thickness as long as the coating is durable and adhesive.

The preferred components for the coating will vary depending upon the type of solvent system used. Therefore, water base coatings and organic base coatings are described in separate sections.

Water-Base Coatings

Water soluble binders that are suitable for use in the present invention include, but are not limited to water soluble polyalkylene oxides and hydroxylated or carboxylated cellulose-derived polymers, including, but not limited to salts of cellulosic acids and carboxyalkyl-derivatives of cellulose, such as carboxyethylcellulose, carboxymethylcellulose, and carboxyhydroxycellulose. A preferred cellulose-derived polymer is hydroxy propylmethyl cellulose, most preferably Grade E5, available from Dow Chemical Co. A preferred polyalkylene oxide is Polyox® Grade N-80, which is available from Union Carbide. Water soluble polyethylene glycols, such as the CARBOWAX™ variety, available from Dow Chemical Co. and Union Carbide, also should operate as water soluble binders in the present invention; however, polyethylene glycols are not preferred binders.

The coating preferably should contain a humectant in order to draw water and water vapor into the coating and to stabilize the water content of the coating at a level sufficient to pull biological contaminants into the lime and to maintain the hydrated lime at an alkalinity effective to kill microorganisms. Suitable humectants for a water base coating include, but are not necessarily limited to, water soluble glycols, such as glycerol, polyethylene glycol and tripropylene glycol. A preferred humectant for water base coatings is glycerol.

Preferably, the coating should contain a plasticizer to facilitate processing and to increase the flexibility and toughness of the final product. Plasticizers are believed to "solvate" the polymer molecules in the coating. Suitable plasticizers for water base coatings also may serve as humectants, and include, but are not necessarily limited to, glycerol and polyols, such as polyethylene glycol and its derivatives. A preferred water-soluble plasticizer is glycerol.

A preferred water base paint is as follows:

| Component | Range of Parts by Weight (Preferred) |
|---|---|
| Binder | 10–30 (20) |
| Hydrated Lime | 10–30 (30) |
| Water | 60–150 (100) |
| Surfactant | 0.5–2 (1) |
| Titanium Oxide | 10–100 (50) |
| Calcium Carbonate | 0–30 (0) |
| Plasticizer (i.e., glycols) | 2–20 (10) |
| Hydrophilic Thickener | 0–2 (1) |
| Pigment | (as desired) |
| Lime:Binder Ratio | 1:1 to 3:1 (1.5:1) |
| Filler:Binder Ratio | 3.5:1 to 9.5:1 (3.5:1) |

Organic Base Coatings

Suitable binders that are soluble in organic solvents include, but are not limited to, cellulose-derived polymers, including but not limited to: alkyl celluloses; cellulose ethers; esters of cellulose, such as cellulose acetate and cellulose butyrate. A preferred binder for use in organic solvents is ethylcellulose. Certain organically soluble polyethylene glycols also could be used as binders in organic base coatings; however, polyethylene glycols are not preferred.

The organic solvent system should have a controllable drying rate to avoid shrinkage or cracks. An organic base coating preferably should comprise between about 2–20 wt % humectant, preferably between about 5–15 wt % humectant. Suitable humectants include organically soluble polyalkylene glycols. A preferred humectant for an organic base coating is propylene glycol.

Suitable plasticizers for organic base coatings include, but are not necessarily limited to, non-volatile organic liquids and low-melting solids, such as phthalate, adipate, and sebacate esters, tricresyl phosphate, castor oil, etc. A preferred plasticizer for this organic base coating is propylene glycol, which also serves as a humectant.

A preferred solvent base paint is as follows:

| Component | Range of Parts by Weight (Preferred) |
|---|---|
| Binder (ethylcellulose) | 10–30 (20) |
| Hydrated Lime | 10–30 (30) |
| Xylene | 50–200 (100) |
| Toluene | 25–100 (50) |
| Ethanol | 0–50 (5) |
| Mineral Spirits | 0–50 (5) |
| Titanium Oxide | 15–100 (50) |
| Calcium Carbonate | 0–30 (5) |
| Plasticizer | 0–10 (5) |
| Hydrophobic Thickener | 2–20 (10) |
| Pigment | (as desired) |
| Lime:Binder Ratio | 1:1 to 3:1 (1.5:1) |
| Filler:Binder Ratio | 3.5:1 to 11.5:1 (3.5:1) |

With the addition of pigments (colorants), other than titanium oxide, or in addition to titanium oxide, the filler ratio will be at the higher end of this scale. In general, very small percentages (2–5 wt % of total recipe) of pigments (colorants) are typically used to provide the tone and shade desired.

Components Useful in Any Solvent Systems

Some of the components of the coating may be used in either a water base or an organic base coating. For example, a filler is reflected in the above formulations, and preferably should be added to extend the coating and to provide inherent structure to the coating to reduce shrinkage and peeling, and to leave a continuous coating after the moisture evaporates. Suitable fillers for use with either solvent system include, but are not necessarily limited to, calcium carbonate, barium sulfates, silicates, glass spheres, hollow microspheres, silica flour, clays, talc, volcanic ash, fly ash, slag, titania, etc. A preferred filler is calcium carbonate.

Pigment or opacifier may be added, if desired, to opacify or add color to the coating. Suitable pigments/opacifiers for use with any of these solvent systems include, but are not necessarily limited to, calcium carbonate, titanium oxide, carbon black, chromium oxide, and iron oxide. Preferred opacifiers are calcium carbonate, which also acts as a filler, and titanium oxide, which also acts as a whitening agent. The pigment/opacifier preferably should comprise about 5–10 parts by weight of the coating.

Ionic and/or non-ionic surfactants of either the wetting agent, detergent, or emulsifier type also may be used to reduce the surface tension and to increase the efficiency of the coating in wetting its ingredients during blending. Suitable surfactants and detergents for use with any of these solvent systems include, but are not necessarily limited to, sodium alkyl and aryl sulfonates (anionic), alkyl phenol ethers of polyethylene glycol (non-ionic), and various cationic agents. Preferred surfactants are Dupanol ME, available from Dupont, Tergitol TMN and Tergitol 15S70, both of which are available from Union Carbide, or Triton X-100, available from Rohm & Haas.

An antifoaming or defoaming agent also may be added, if desired, for ease in processing. Suitable antifoaming agents for use with any of these solvent systems include, but are not necessarily limited to, sulfonated oils, organic phosphates, silicone fluids, dimethylpolysiloxanes, etc. Preferred antifoaming agents are Dow Corning Antifoam Agent DB-31, SG-10, 1510US, 544 compound, DB110A, and similar antifoaming agents, all of which are commercially available from Dow Corning. A most preferred antifoaming agent is SG-10, available from Dow Corning.

Whether water base or organic base, the biocidal coating preferably should be applied to a thickness of between about 2–5 mils to assure long term biocidal activity of the lime. However, a thinner or thicker coating may be used.

In the paint industry, considerable latitude is taken to affect paints or coatings of varied textures, colors, and luster or flat appearance. Such practice can be applied to these basic recipes without altering their antimicrobial performance and their durability with respect to carbon dioxide resistance providing they do not transcend the critical lime to binder ratios and pigment to binder ratios expressed within the parenthetical ranges. The ranges given in the foregoing formulas allow for such latitude in the practice of preferred paint, texture, color, and application techniques.

Separate Protective Coatings Incorporating a Non-Water Soluble Binder

Some concern exists that water base coatings or paints might be less durable than organic base coatings over the long term because of repeated washings, wipings, etc. One way to prolong the life of substantially any hydrated lime coating, including a water base coating, is to provide the coating with a protective film comprising one of the non-water soluble, or organically soluble binders listed above.

A non-water soluble binder in a separate, protective film should provide substantially the same protection for the underlying lime coating as the protection afforded when the binder is incorporated directly into the lime coating. The binder in the protective film should prevent carbon dioxide from reacting with the lime in the underlying coating, and should allow moisture to permeate into the coating.

In a preferred embodiment, the protective film comprises between about 5–15 wt % of a non-water soluble cellulose-derived polymer dissolved in between about 85–95 wt % of an appropriate organic solvent, preferably a volatile organic solvent. The protective film preferably should be sprayed or otherwise deposited in a fine mist over the water-base coating to assure adequate coverage and protection of the coating.

The invention will be better understood with reference to the following examples:

EXAMPLE 1

Organic base coatings containing ethylcellulose as a binder were prepared using the following components:

| | |
|---|---|
| Ethylcellulose (ETHOCEL ™, obtained from Dow Chemical) | 5–20 parts by weight |
| Toluene | 30 parts by weight |
| Xylene | 50 parts by weight |
| Ethanol | 20 parts by weight |
| Calcium Hydroxide | 50 parts by weight |
| Titanium Oxide | 50 parts by weight |
| Propylene Glycol | 5–15 parts by weight |

The coatings were spread to a thickness of between about 2–5 mil onto various substrates, including concrete, Plaster of Paris, aluminum, stainless steel, plastics, etc. The coated substrates were maintained for ten weeks in a Q-Panel Co. Ultraviolet Weatherometer exposed to UV light having a wavelength of 350 nm U.V.B. at 50 percent relative humidity. Before and after the exposure, the pH of the coatings was about 12.3 (measured as described in Example 2). These results indicate that the coating should have good stability when exposed to sunlight, humidity and atmosphere. The coating also was visually inspected for cracks and manually inspected for lift, peel off, and/or delamination when the substrate was flexed. The coating exhibited good adhesion.

EXAMPLE 2

All compositions herein evolved from a series of empirical screening tests seeking optimum film integrity and activity values. Water base coatings containing different test binders were prepared using the following ranges of components:

| | |
|---|---|
| Binder | 5, 10, and 15 parts by weight |
| Water | 100 parts by weight |
| Calcium Hydroxide | 10–50 parts by weight |
| Calcium Carbonate | 50–150 parts by weight |
| Titanium Oxide | 0–15 parts by weight |
| Modifiers | 5–15 parts by weight |

"Modifiers" refers to surfactants, anti-foam agents, plasticizers, and humectants, combined. The binders tested were:

PolyOx™ (polyethylene oxide, Union Carbide);
Hydroxy ethyl cellulose (HEC), obtained from Hercules, Inc.;

Hydroxy propyl methyl cellulose (HPMC), obtained from Hercules, Inc.;

Ethyl hydroxy ethyl cellulose (EHEC), obtained from Hercules, Inc.;

Carboxy methyl hydroxyethyl cellulose (CMHEC), obtained from Hercules, Inc.;

Carboxy methyl cellulose (CMC), obtained from Dow Chemical.

The coatings were spread onto various substrates, including concrete, Plaster of Paris, aluminum, stainless steel, plastics, etc., to a thickness of between about 2–5 mil, typically about 3 mil. The coated substrates were subjected to accelerated aging by maintaining the substrates for ten weeks in a Q-Panel Co. Ultraviolet Weatherometer exposed to UV light having a wavelength of 350 nm U.V.B. at 50 percent relative humidity. Each day of such exposure was equivalent to approximately 15 days of exposure to sunlight. The pH of the coatings was measured before and after the test. A sample of the coating was suspended in water and the pH was tested using a pH meter. Before and after the exposure, the pH was about 12.3. These results indicate that the coatings have good stability when exposed to sunlight, humidity and atmosphere (about 6% carbon dioxide). The coatings also were visually inspected for cracks and manually inspected for lift, peel off, and/or delamination when the substrate was flexed. The coatings exhibited good adhesion.

EXAMPLE 3

Coatings containing the components listed in Example 2 were made using the following binders:

PolyOx™ (polyethylene oxide, Union Carbide);

Hydroxy ethyl cellulose (HEC), obtained from Hercules, Inc.;

Hydroxy propyl methyl cellulose (HPMC), obtained from Hercules, Inc.

A 2–5 mil thick coating of each sample was applied to spun bonded resin. Discs were cut from the coated, spun-bonded resin and laid on tryptic soy auger. Suspensions of log-phase bacteria, namely $E.$ $coli$ or P-aeruginosa, and fungi, namely Aspergillus, were centrifuged from their growth media and then resuspended in sterile water. The discs were flooded with suspended bacteria and fungi, and the flooded discs were incubated for 72 hours at 37° C. (98.6° C.) (others at room temperature), and visually inspected before and after staining with Gram's Stain. No biological growth of bacteria was observed.

The absence of biological growth in these tests is noteworthy. Most tests of the biocidal activity of lime are performed by immersing test specimens containing cultures of microorganisms (i.e., fruit laden with bacteria) into a supernatant fluid of a saturated lime solution. In contrast, these tests relied on the relatively dry, solid surface of the coating or "paint" to prevent bacterial and fungal activity.

The water base coatings did exhibit a tendency to rub off when a wet cloth was abrasively applied to the coatings. The coatings made with PolyOx™ at 17 pt/wt and hydroxy propyl methyl cellulose (HPMC) at 10–15 pt/wt were least likely to rub out upon application of a wet cloth.

EXAMPLE 4

Spun bonded resin was coated with a 2–5 mil-thick coating containing the components listed in Example 2. Discs were cut from the coated, spun-bonded resin and laid on tryptic soy auger. Suspensions of log-phase bacteria, namely $E.$ $coli$ or P-aeruginosa, and fungi, namely Aspergillus were centrifuged from their growth media and then resuspended in sterile water. The discs were flooded with suspended bacteria and fungi, and the flooded discs were incubated for 72 hours at 37° C. (98.6° C.) (others at room temperature), and visually inspected before and after staining with Gram's Saffranin. No biological growth of bacteria was observed.

EXAMPLE 5

A protective film was prepared by mixing 10 wt % ethylcellulose in acetone. The film was sprayed in a fine mist onto substrates bearing 3 mil coatings having the formulation described in Example 2 with the following binders:

PolyOx™ (polyethylene oxide, Union Carbide); and,

Hydroxy propyl methyl cellulose (HPMC), obtained from Hercules, Inc.;

The ethylcellulose/acetone mixture was applied to a thickness of about 0.5 mil. After the ethylcelluloselacetone mixture dried, the surface was rubbed with a wet, red rag. The rag did not lift any lime from the surface, as evidenced by the absence of white contaminant on the rag.

EXAMPLE 6

The coating of Example 2 was subjected to continued accelerated aging for the equivalent of four years simulated exposure. The coating was again analyzed for biocidal activity and alkalinity as described in Example 2. Slight changes were seen during the first month of exposure, after which the coating appeared to stabilize. After four years of simulated exposure, chemical analysis of the coatings indicated active performance of at least about 70% of the lime's original content and 100% of the biocidal activity level.

EXAMPLE 7

A coating was prepared having the following composition:

| Component | Range of Parts by Weight |
| --- | --- |
| Binder (ethylcellulose) | 10 |
| Hydrated Lime | 15 |
| Xylene | 100 |
| Toluene | 50 |
| Ethanol | 5 |
| Mineral Spirits | 5 |
| Titanium Oxide | 20 |
| Calcium Carbonate | 0 |
| Plasticizer | 5 |
| Hydrophobic Thickener | 1 |
| Pigment | (as desired) |
| Lime:Binder Ratio | 1:5:1 |
| Filler:Binder Ratio | 3.5:1 |

A single coat of the foregoing coating was applied over a mildew-blackened outdoor building surface. After nearly four years, the surface remains a pristine white, and chemical analysis of the coating indicated active performance of 72% of the limes original content and 100% of the biocidal activity level.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

We claim:

1. A biocidal coating composition comprising:
   (a) hydrated lime, and
   (b) an organic soluble or water soluble binder polymer mixture; said mixture consisting essentially of a cellulosic polymer and a polyalkylene oxide and forming a film permeable to water and impermeable to carbon dioxide;
   the ratio, in parts by weight, of said lime to said binder polymer mixture being about 1:1 to 3:1 and wherein the total quantity of solids in said composition is insufficient to disrupt continuity of said film thereby permitting said film to act as an effective barrier against carbon dioxide.

2. The biocidal coating composition of claim 1 including a humectant.

3. The biocidal coating composition of claim 2 wherein the humectant is present in an amount effective to maintain moisture in said coating sufficient to pull biological contaminants into contact with said lime and to maintain said hydrated lime at an alkalinity effective to kill microorganisms.

4. A biocidal paint comprising:
   (a) hydrated lime, and
   (b) an organic soluble or water soluble binder polymer mixture; said mixture consisting essentially of a cellulosic polymer and a polyalkylene oxide and forming a film permeable to water and impermeable to carbon dioxide; the ratio, in parts by weight, of said lime to said binder polymer mixture being about 1:1 to 3:1 and wherein the total quantity of solids in said composition is insufficient to disrupt continuity of said film thereby permitting said film to act as an effective barrier against carbon dioxide.

5. The biocidal paint of claim 4 including a humectant.

6. The biocidal paint of claim 5 wherein the humectant is present in an amount effective to maintain moisture in said coating sufficient to pull biological contaminants into contact with solid lime and to maintain said hydrated lime at an alkalinity effective to kill microorganisms.

7. A substrate surface comprising a biocidal coating wherein said coating comprises:
   (a) hydrated lime, and
   (b) an organic soluble or water soluble binder polymer mixture; said mixture consisting essentially of a cellulosic polymer and a polyalkylene oxide and forming a film permeable to water and impermeable to carbon dioxide; the ratio, in parts by weight, of said lime to said binder polymer mixture being about 1:1 to 3:1 and wherein the total quantity of solids in said composition is insufficient to disrupt continuity of said film thereby permitting said film to act as an effective barrier against carbon dioxide.

8. The substrate surface of claim 7 wherein said biocidal coating includes a humectant.

9. The substrate surface of claim 8 wherein the humectant is present in an amount effective to maintain moisture in said coating sufficient to pull biological contaminants into contact with said lime and to maintain said hydrated lime at an alkalinity effective to kill microorganisms.

10. The biocidal coating composition of claim 1 wherein said polyalkylene oxide is a polyethylene oxide.

11. The biocidal coating composition of claim 1 wherein said cellulosic polymer is ethylcellulose or hydroxypropylmethyl cellulose and said polyalkylene oxide is a polyethylene oxide.

12. The biocidal paint of claim 4 wherein said polyalkylene oxide is a polyethylene oxide.

13. The biocidal paint of claim 4 wherein said cellulosic polymer is ethylcellulose or hydroxypropylmethyl cellulose and said polyalkylene oxide is a polyethylene oxide.

14. The substrate surface of claim 7 wherein said polyalkylene oxide is polyethylene oxide.

15. The substrate surface of claim 7 wherein said cellulosic polymer is ethylcellulose or hydroxypropylmethyl cellulose and said polyalkylene oxide is a polyethylene oxide.

16. The coating composition of claim 1 wherein said cellulosic polymer is selected from the group consisting of ethylcellulose and hydroxy propylmethyl cellulose.

17. The paint of claim 4 wherein said cellulosic polymer is selected from the group consisting of ethylcellulose and hydroxy propylmethyl cellulose.

18. The substrate surface of claim 7 wherein said cellulosic polymer is selected from the group consisting of ethylcellulose and hydroxy propylmethyl cellulose.

* * * * *